(12) United States Patent
Van Den Bossche

(10) Patent No.: US 11,137,329 B2
(45) Date of Patent: Oct. 5, 2021

(54) APPARATUS AND METHOD FOR PERFORMING AN IMPACT EXCITATION TECHNIQUE

(71) Applicant: GRINDOSONIC BVBA, Leuven (BE)

(72) Inventor: Alex Van Den Bossche, Neerijse (BE)

(73) Assignee: GRINDOSONIC BV, Leuven (BE)

( * ) Notice: Subject to any disclaimer, the term of this patent is extended or adjusted under 35 U.S.C. 154(b) by 98 days.

(21) Appl. No.: 16/633,786

(22) PCT Filed: Jul. 27, 2018

(86) PCT No.: PCT/EP2018/070518
§ 371 (c)(1),
(2) Date: Jan. 24, 2020

(87) PCT Pub. No.: WO2019/020825
PCT Pub. Date: Jan. 31, 2019

(65) Prior Publication Data
US 2021/0088432 A1    Mar. 25, 2021

(30) Foreign Application Priority Data

Jul. 27, 2017 (EP) .................................... 17183649

(51) Int. Cl.
*G01N 3/34* (2006.01)
*G01N 3/40* (2006.01)
*G01N 33/00* (2006.01)

(52) U.S. Cl.
CPC ............... *G01N 3/34* (2013.01); *G01N 3/405* (2013.01); *G01N 2033/0078* (2013.01)

(58) Field of Classification Search
CPC ............ G01N 3/32; G01N 3/34; G01N 3/405; G01N 2203/0078
See application file for complete search history.

(56) References Cited

U.S. PATENT DOCUMENTS

2014/0074411 A1   3/2014   Phillips et al.
2016/0011088 A1   1/2016   Guthrie et al.

FOREIGN PATENT DOCUMENTS

| EP | 3141305 A1 | 3/2017 |
| WO | 2009060392 A1 | 5/2009 |
| WO | 2012040584 A1 | 3/2012 |

OTHER PUBLICATIONS

Provencher, "A Fourier Method for the Analysis of Exponential Decay Curves," Biophysical Journal, vol. 16, 1976, pp. 27-41.
(Continued)

*Primary Examiner* — Erika J Villaluna
(74) *Attorney, Agent, or Firm* — Workman Nydegger

(57) ABSTRACT

The invention pertains to an apparatus for analyzing a mechanical vibratory response of a solid material sample, the apparatus comprising: an array of impactors arranged to impart an impact on respective well-defined points on the surface of said solid material sample; a sensor configured to capture said mechanical vibratory response as a time-varying signal, subsequent to an impact of said at least one impactor; and processing means configured to analyze said time-varying signal to determine the frequencies and decay constants of sinusoids making up said time-varying signal. The invention also pertains to a corresponding method of characterizing a solid material sample.

18 Claims, 3 Drawing Sheets

(56) References Cited

OTHER PUBLICATIONS

Mandelshtam et al., "Harmonic Inversion of Time Signals and its Applications," Journal of Chemical Physics, vol. 107, No. 17, Nov. 1, 1997, pp. 6756-6770.
Jasim et al., "Characterisation of Mechanical Properties Using I-Kaz Analysis Method under Steel Ball Excitation Technique," Journal of Applied Sciences, vol. 14, No. 24, Oct. 21, 2014, pp. 3595-3603.
Benko et al., "Using Filter Diagonalization for Fault Detection in Low-Speed Rotational Machinery," Fault Detection, Supervision and Safety of Technical Processes 2006, Jan. 1, 2007, Department of Systems and Control, Jozef Stefan Institute, pp. 1342-1347.
International Preliminary Report on Patentability from PCT Application No. PCT/EP2018/070518, dated Aug. 13, 2019.
International Search Report from PCT Application No. PCT/EP2018/070518, dated Oct. 30, 2018.
European Search Report from Application No. EP17183649, dated Nov. 23, 2017.

APPARATUS AND METHOD FOR PERFORMING AN IMPACT EXCITATION TECHNIQUE

FIELD OF THE INVENTION

The present invention pertains to the field of impact excitation technique, in particular to determine the elastic properties and internal friction of a material of interest.

BACKGROUND

Impulse excitation techniques are used to determine certain physical properties of a sample of a material of interest, by impacting the sample with a dedicated tool or projectile, and analyzing the resulting vibrations as they are picked up with a sensor such as a piezoelectric sensor, a microphone, a laser vibrometer or an accelerometer. The vibration signal is transformed to the frequency domain by a Fourier transform, to identify the resonant frequency, which, together with the geometry of the sample, permit calculation of the elastic properties of the material. The technique is generally non-destructive, and may be applied at room temperature or at a different chosen (typically elevated) test temperature.

Various methods and apparatus are known to perform material analysis according to impulse excitation technique. For example, European patent application publication no. EP 3 141 305 A, entitled "Experimental method to detect the elastic modulus of objects, samples or semi-worked products of various materials", in the name of Universitá degli Studi di Trieste, discloses an experimental method to detect the elastic modulus (E) of objects, samples, or semi-worked products, comprising the step of imparting a mechanical stress to the sample object by means of an impact generated by a beating element with respect to an inertial body; introducing an exciting body of predetermined mass (m) between the beating element and the sample object so that the exciting body is disposed in contact with the sample object in correspondence with a contact surface having a predetermined extension value; imparting the mechanical stress on the sample object by impacting the beating element on the exciting body; acquiring a response signal corresponding to an elongation variation (X) of the sample object; processing a value of the elastic modulus (E) of the sample object as a function at least of the extension value (S) of the contact surface and the value of an elongation variation (X) of the sample object.

It is a disadvantage of the known methods and apparatus that the detected resonance frequency is not suitable by itself to signal and characterize the various types of defects (such as cracks or fissures) that may occur in industrially produced objects, samples or semi-worked products of various materials.

It is an object of embodiments of the present invention to at least partially overcome the disadvantages of the prior art.

SUMMARY

According to an aspect of the present invention, there is provided an apparatus for analyzing a mechanical vibratory response of a solid material sample, the apparatus comprising: an array of impactors arranged on a line to impart an impact on respective well-defined points on the surface of said solid material sample and means to cause a relative movement of said solid material sample and said array of impactors in a direction substantially perpendicular to said line, or an array of impactors arranged in a grid; a sensor configured to capture said mechanical vibratory response as a time-varying signal, subsequent to each impact of said array of impactors; and processing means configured to analyze said time-varying signal to determine the frequencies and decay constants of sinusoids making up said time-varying signal.

The invention is based inter alia on the inventive insight of the inventor that the response of a solid sample under test to an impact excitation is physically close to a sum of exponentially decaying sinusoids. By assuming this particular mathematical form of the excitation response, based on the underlying physics of the phenomenon, better accuracy can be obtained than by simply extracting peaks in the (fast) Fourier transform. The invention is further based on the insight that the decay constants provide more insight in the presence of defects than the mere identification of the resonance frequency of the sample under test. The invention is further based on the insight that the identification of the decay constants constitutes a harmonic inversion problem, which can be solved by known mathematical methods.

It is an advantage of the invention that the apparatus can be used in a scanning mode to test local material properties in larger samples, whereby the impactors (all of them or selected ones) are activated consecutively along the line prior to moving the line relatively to the sample and repeating the procedure, thus effectively analyzing the sample on a grid of points. For each individual impact, the response may be captured and analyzed, to obtain information about the material properties in the immediate vicinity of the impact point.

The apparatus may be implemented in a housing having the impactors arranged therein in a fixed position, and provided with means to linearly move the sample underneath the fixedly arranged impactors so as to allow the impactors to reach all points of interest on the surface of the sample.

Alternatively, the apparatus may be implemented in a housing receiving the sample therein in a fixed position, and provided with means to linearly move the impactors over the fixedly arranged sample so as to allow the impactors to reach all points of interest on the surface of the sample.

If the array of impactors is arranged in a grid, the apparatus can be used to test local material properties in larger samples, without requiring relative motion of the sample and the apparatus, whereby the impactors (all of them or selected ones) are activated consecutively along the grid. For each individual impact, the response may be captured and analyzed, to obtain information about the material properties in the immediate vicinity of the impact point.

It must be noted that it is also possible to apply relative movement between the sample and the array of impactors in the case of a grid-based arrangement, in order to analyze the sample on a larger and/or denser grid of points than would be possible when operating from a single sample position.

In an embodiment of the apparatus according to the present invention, the processing means is further configured to detect a material defect in the solid material sample on the basis of said determined frequencies and decay constants.

As the apparatus of the present invention provides excitation response information of the sample at various points along the surface of the sample, it becomes possible to detect the presence of material defects, as these will cause anomalous responses.

In an embodiment, the apparatus according to the present invention is further configured to cause a relative movement of said solid material sample and said array of impactors along two axes.

It is an advantage of this embodiment that measurements can be taken at point that lie in between the lines defined by the main scanning direction, leading to a higher level of accuracy of the spatial localization of defects.

In an embodiment, the apparatus according to the present invention further comprises supports configured to support said solid material sample at nodes of a vibration mode to be excited.

It is an inventive insight of the inventors that by placing the sample under test on supports that coincide with nodes (zeros) of the vibration mode to be excited, a more accurate response signal can be obtained. The means for moving the sample relative to the array of impactors is arranged to ensure that the sample remains supported on the selected nodes notwithstanding the movement.

In an embodiment, the apparatus according to the present invention further comprises one or more of a temperature sensor, means to determine geometric properties of the solid material sample, and a scale.

It is an advantage of including a temperature sensor that the physical properties of interest can more easily be analyzed under different thermal circumstances, whereby the temperature is measured at the same time as the time-varying signal; this may include the identification of thermally induced material transitions. The temperature sensor and the mechanical vibration sensor may be integrated in the same probe. It is an advantage of including means to determine geometric properties and/or a scale that the size and density of the sample can be accurately detected, said variables being necessary to convert the obtained resonance properties into physical material properties such as a Young's modulus (E) or a shear modulus (G).

In an embodiment of the apparatus according to the present invention, the sensor is equipped with means to illuminate a spot where the mechanical vibratory response is captured.

It is an advantage of this embodiment that the user can be aided in precisely locating the desired location for capturing the response, which improves the reproducibility of the performed measurement.

In an embodiment of the apparatus according to the present invention, the sensor is a contact-based sensor equipped with means to measure a force applied by the sensor on said solid material sample.

It is an advantage of this embodiment that, when using a contact-based sensor such as a piezoelectric sensor, the user can be aided in precisely applying a desired amount of force during the capturing of the response, which improves the reproducibility of the performed measurement.

In an embodiment of the apparatus according to the present invention, the processing means is configured to solve a harmonic inversion problem by applying a general filter-diagonalization method.

According to an aspect of the present invention, there is provided a method of characterizing a solid material sample, the method comprising: imparting an impact on a plurality of well-defined points on the surface of said solid material sample, by using an array of impactors arranged on a line and moving said solid material sample relative to said array of impactors in a direction substantially perpendicular to said line, or by using an array of impactors arranged on a grid; capturing a mechanical vibratory response as a time-varying signal, subsequent to said imparting of each such imparted impact; and analyzing said time-varying signal to determine the frequencies and decay constants of sinusoids making up said time-varying signal.

It is an advantage of the invention that the apparatus can be used in a scanning mode to test local material properties in larger samples, either by activating impactors (all of them or selected ones) consecutively along a line prior to moving the line relatively to the sample and repeating the procedure, or by activating impactors (all of them or selected ones) consecutively along a grid, thus effectively analyzing the sample on a grid of points. For each individual impact, the response may be captured and analyzed, to obtain information about the material properties in the immediate vicinity of the impact point.

The method may be implemented by using an apparatus disposed in a housing having the impactors arranged therein in a fixed position, and provided with means to linearly move the sample underneath the fixedly arranged impactors so as to allow the impactors to reach all points of interest on the surface of the sample.

Alternatively, the method may be implemented by using an apparatus disposed in a receiving the sample therein in a fixed position, and provided with means to linearly move the impactors over the fixedly arranged sample so as to allow the impactors to reach all points of interest on the surface of the sample.

Alternatively, the method may be implemented by using an apparatus with an array of impactors arranged in a grid, which may or may not be moved relative to the solid material sample.

In an embodiment, the method further comprises detecting a material defect in said solid material sample (99) on the basis of said determined frequencies and decay constants.

In an embodiment, the method according to the present invention further comprises placing the solid material sample on supports coinciding with nodes of the vibration mode to be excited.

In an embodiment, the method according to the present invention further comprises estimating a location of a defect on the basis of said frequencies and decay constants obtained for different impact positions.

It is an advantage of the present invention that it can provide information about material properties at a large number of densely spaced grid points. Thus anomalies detected at some of those grid points but not at others provide an insight about the estimated location of a material defect such as a crack or a fissure.

In an embodiment of the method according to the present invention, said analyzing further comprises determining a dynamic Young's modulus (E) from said frequencies.

In an embodiment of the method according to the present invention, said analyzing further comprises determining a shear modulus (G) from said frequencies.

In an embodiment of the method according to the present invention, said analyzing further comprises comparing said decay constants to reference values.

In an embodiment of the apparatus according to the present invention, said analyzing comprises solving a harmonic inversion problem by applying a general filter-diagonalization method.

According to an aspect of the present invention, there is provided a method of controlling a quality of an article of manufacture, the method comprising: characterizing at least a part of said article of manufacture as said solid material sample using the method as described above; signaling a "pass" condition if said decay constants are within a predetermined margin of said reference values; and declaring a "fail" condition if said decay constants are outside said predetermined margin of said reference values.

According to an aspect of the present invention, there is provided a computer program product comprising code means configured to cause a processor to carry out the computation steps of the method as described above.

In an embodiment of the computer program product according to the present invention, the code means comprises the Harminv program.

The technical effects and advantages of embodiments of the methods and the computer program product according to the present invention correspond, mutatis mutandis, to those of the corresponding embodiments of the apparatus according to the present invention.

BRIEF DESCRIPTION OF THE FIGURES

These and other features and advantages of embodiments of the present invention will now be described in more detail with reference to the attached drawings, in which.

DESCRIPTION OF EMBODIMENTS

In known Impact Excitation Technique (IET) procedures, the sample under test is positioned in such a way that it can vibrate substantially unhindered upon being impacted. This is achieved by placing the sample on a piece of lightweight foam or resting it on linear supports (e.g. wires or narrow bars) that are judiciously placed under the zeros (nodes) of the vibration mode to be excited. The excitation is performed by impacting the sample at an anti-node, i.e. a point where the local amplitude of the induced motion is maximal for the mode of interest.

Figure 1:
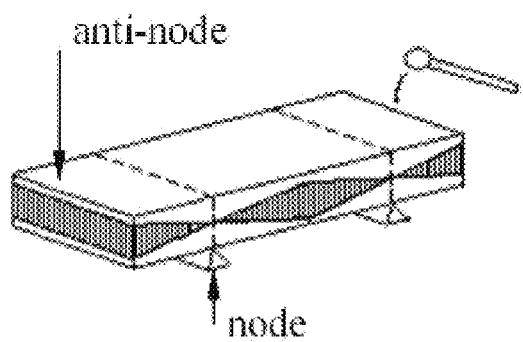
FIG. 1 schematically illustrates the vibration induced in a beam-shaped sample upon excitation in the flexure mode.

FIG. 1 schematically illustrates the vibration induced in a beam-shaped sample under test upon excitation in the flexure (in particular, out-of-plane vibration) mode. The eigenfrequency $f_f$ of this vibration mode is indicative of the sample's dynamic Young's modulus E. For the illustrated beam with mass m, length L, width b, and thickness t, one may use the following relation:

$$E = 0.9465 \left( \frac{mf_f^2}{b} \right) \left( \frac{L^3}{t^3} \right) T$$

with the correction factor T defined as $$T = 1 + 6.585 \left( \frac{t}{L} \right)^2 \text{ if } L/t \geq 20.$$

Figure 2:
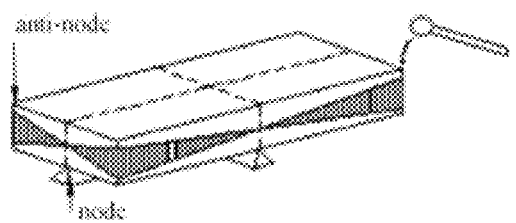
FIG. 2 schematically illustrates the vibration induced in a beam-shaped sample upon excitation in the torsion mode.

FIG. 2 schematically illustrates the vibration induced in a beam-shaped sample under test upon excitation in the torsion mode. The eigenfrequency $f_t$ of this vibration mode is indicative of the sample's shear modulus. For the illustrated beam with mass m, length L, width b, and thickness t, one may use the following relation:

$$G = \frac{4Lmf_t^2}{bt} R$$

with the correction factor R defined as $$T = \left[ \frac{1 + \left( \frac{b}{t} \right)^2}{4 - 2.521 \frac{t}{b} \left( 1 - \frac{1.991}{e^{\pi \frac{b}{t}} + 1} \right)} \right] \left[ 1 + \frac{0.00851 b^2}{L^2} \right] - 0.060 \left( \frac{b}{L} \right)^{\frac{3}{2}} \left( \frac{b}{t} - 1 \right)^2.$$

These known ways to determine E and G rely only on the peak frequencies in the spectrum of the sample's response. While a shift in E and/or G relative to the expected values may be indicative of a defect in the sample, the inventor has found that an abnormally fast decay of certain frequency components is a more reliable predictor of such defects.

Figure 3:
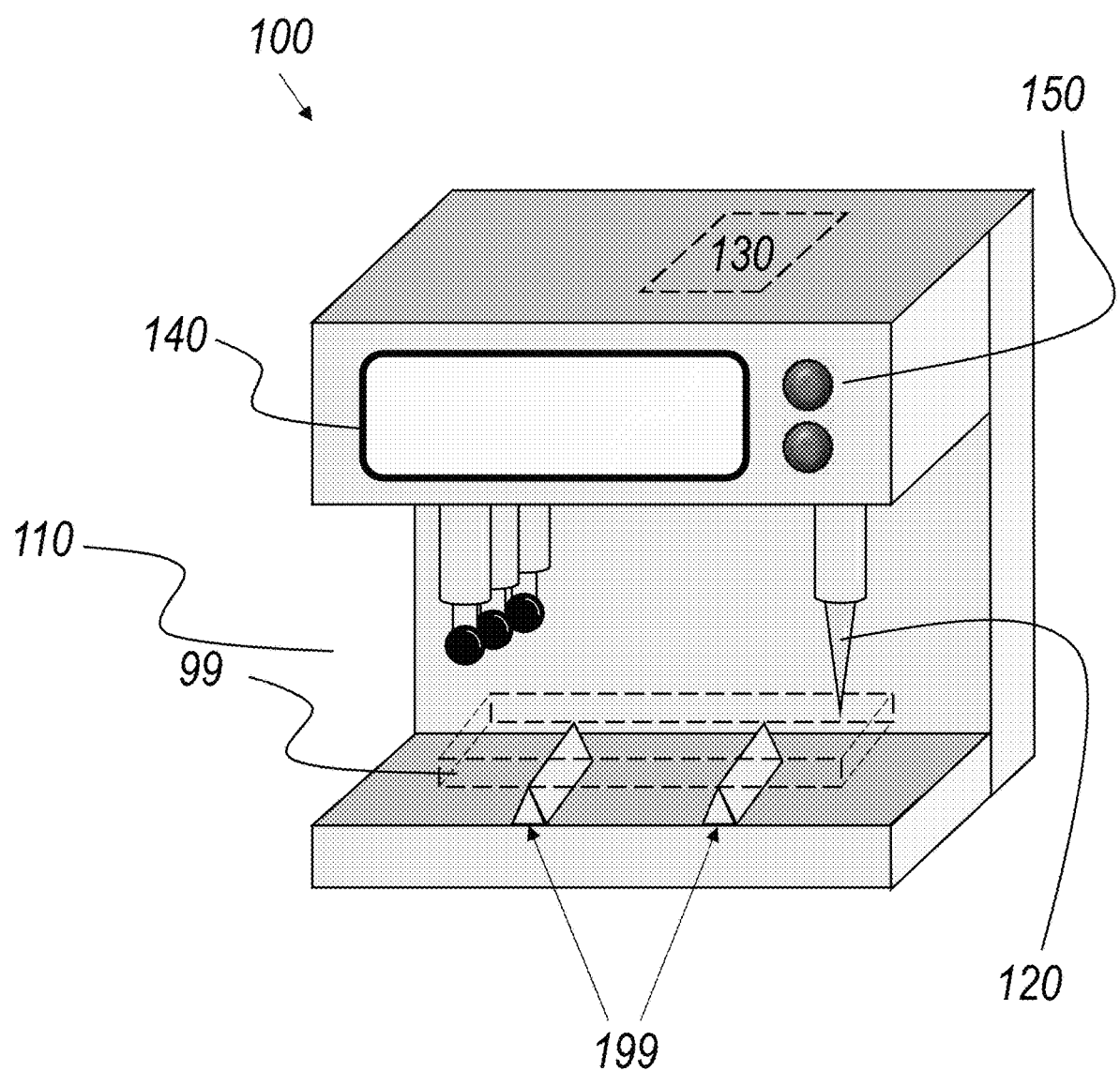
FIG. 3 schematically illustrates an embodiment of the apparatus according to the present invention.
Figure 4:
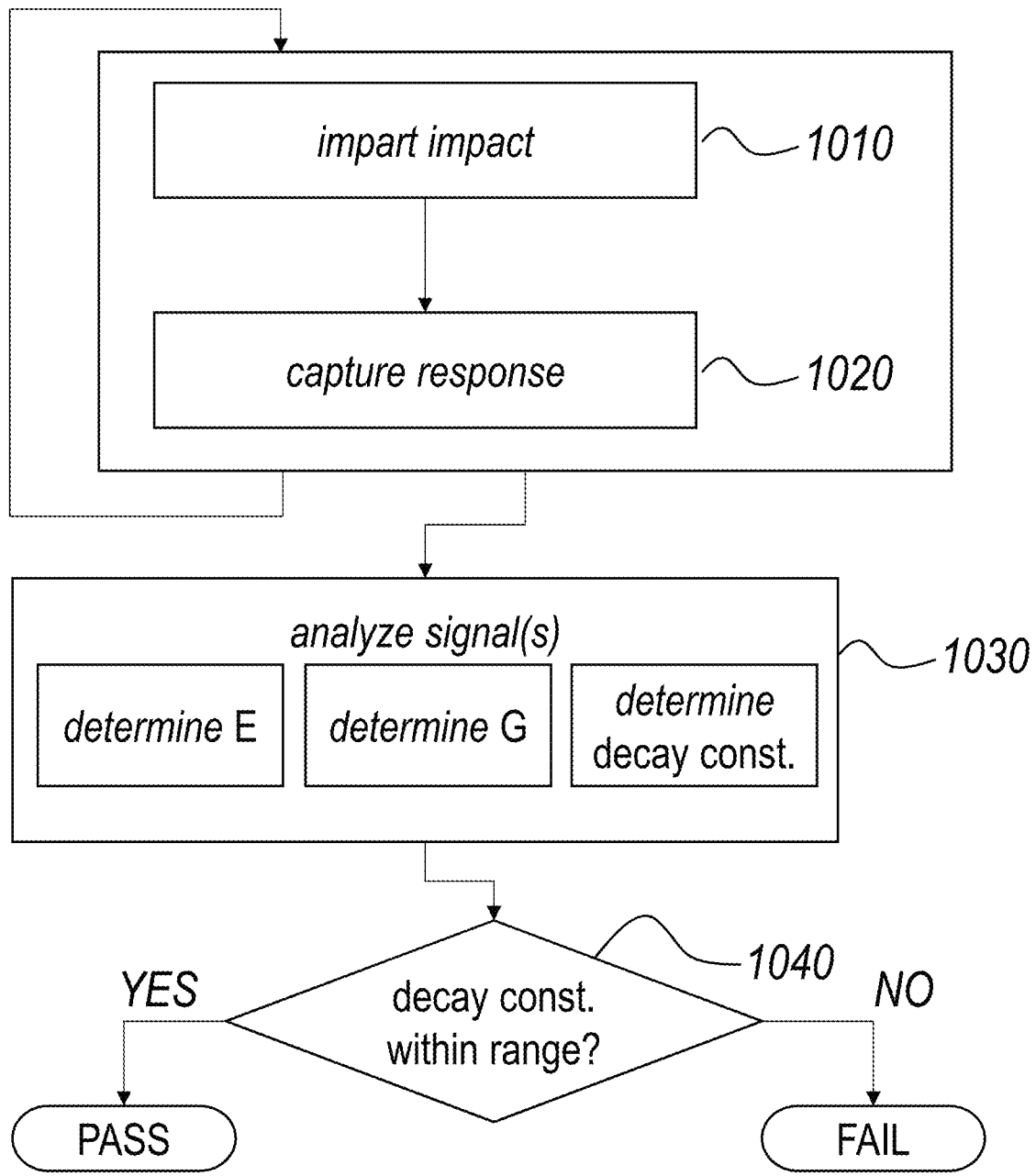
FIG. 4 provides a flow chart of an embodiment of the method according to the present invention.

The present invention provides an apparatus for analyzing a mechanical vibratory response of a solid material sample, an embodiment of which is schematically illustrated in FIG. 3. The apparatus 100 comprises at an array of impactors 110 arranged on a line or a grid to impart an impact on respective well-defined points on the surface of the solid material sample 99.

Without loss of generality, an apparatus 100 with three impactors 110 arranged on a line is illustrated. The apparatus 100 further comprises a sensor 120 configured to capture the mechanical vibratory response of the sample 99 as a time-varying signal, subsequent to an impact of an impactor 110. A suitable sample holder 199, for example comprising linear supports, is provided to allow the sample 99 to freely vibrate upon impact. The apparatus 100 further comprises processing means 130 configured to analyze the time-varying signal to determine the frequencies and decay constants of sinusoids making up the time-varying signal.

The impactors 110 may comprise one or more hammers that are preferably attached to the rest of the apparatus and automatically operated (i.e., weights mounted on an actuated, optionally spring-loaded arm) or other projectiles. The sensor 120 may comprise a contact-based sensor such as a piezoelectric sensor, a non-contact-based sensor such as a microphone or a laser vibrometer, or an accelerometer.

The inventor has found that good results can be obtained with a contact-based sensor such as a piezoelectric sensor, which is less susceptible to environmental disturbances (especially in an industrial environment) than a microphone. The piezoelectric sensor may be arranged in a probe that may further include a signal amplifier, means to illuminate a spot where the mechanical vibratory response is captured (e.g., a small laser source arranged to illuminate the anticipated point of contact with a spot of light as the probe is brought towards the surface of the sample), and/or a temperature sensor. The probe is preferably equipped with means to measure the force applied by the sensor on the sample.

The apparatus may include means to automatically bring the probe in contact with the sample, such as an actuated arm or a more complex robotic support. In this case, the force measuring means provide the necessary feedback to ensure a good contact between the sensor and the sample. If the probe is to be handled manually be the user, the apparatus may be configured to provide visual and/or auditory feedback to help the user keep the contact force within a predetermined target range (for example, an LED may be made to light up in one color when the applied force is too high, and in another color when it is too low; an intermittent beeping sound may have a different pitch or period depending on whether the applied force is too high or too low; etc.).

The impactors may be arranged as a linear array or as a rectangular grid. In the linear case, the apparatus may act as a scanner, moving the sample under the line of impactors for consecutive tests on different parts of the sample, or moving the line of impactors across the sample for consecutive tests on different parts of the sample. The apparatus is preferably equipped with precisely controllable motors to provide the required relative movement of the sample and the impactors. Where the impactors are arranged as a grid, such relative movement will only be necessary if the extent of the grid does not cover the entire area of interest of the sample, or if a higher point density is desired.

The apparatus according to the present invention may be configured to be able to cause a relative movement of said solid material sample and said array of impactors along two axes. This allows the apparatus to provide, in addition to the main scanning movement, a transverse movement that accesses points on the surface of the This will lead to a higher level of accuracy of the spatial localization of defects.

The apparatus preferably comprises means to determine geometric properties of the solid material sample (not illustrated), such as a 3D scanner, a camera (optionally stereoscopic), or the like. As is clear from the formulas provided above, accurate knowledge of the geometry of the sample is important to derive the correct values of the Young's modulus and the shear modulus from the detected frequency peaks. A scale (not illustrated) may be integrated in the apparatus to determine the weight, and hence the mass, of the sample. As is clear from the formulas provided above, accurate knowledge of the mass of the sample is also important to derive the correct values of the Young's modulus and the shear modulus from the detected frequency peaks.

The apparatus 100 may comprise a conventional user interface, which may include a screen 140 (preferably a touch-screen), buttons or dials 150, a keypad (not illustrated), and the like.

The processing means is configured to analyze the time-varying signal to determine the frequencies and decay constants of sinusoids making up the time-varying signal, i.e. it solves a harmonic inversion problem. The problem of a harmonic inversion, which more generally consists of determining frequencies, decay constants, amplitudes, and phases of the sinusoids making up a discrete-time, finite-length signal that consists of a sum of a finite number of such sinusoids in a given bandwidth, is well known in literature, but has not been associated with IET to date. Vladimir A. Mandelshtam and Howard S. Taylor have described the use of the general filter-diagonalization method of Wall and Neuhauser to solve this problem by recasting the harmonic inversion problem as the one of a small matrix diagonalization in their seminal paper "Harmonic inversion of time signals and its applications", *The Journal of Chemical Physics* 107, 6756 (1997). Computer-based implementations of this technique are known in the art, including the "Harminv" program by Steven G. Johnson of the Massachusetts Institute of Technology. The result of the analysis may be output to the screen 140 or to any other suitable interface for storage or further processing by other equipment.

The processing means may consist of one or more dedicated hardware components (e.g. ASIC), appropriately configured configurable hardware components (e.g. FPGA), microprocessors provided with suitable software, or a combination of the above. The same components may also perform other functions.

The present invention also provides a method of characterizing a solid material sample, the method comprising:
imparting an impact 1010 on a plurality of well-defined points on the surface of said solid material sample;
capturing a mechanical vibratory response 1020 as a time-varying signal, subsequent to said imparting of each such imparted impact; and
analyzing said time-varying signal 1030 to determine the frequencies and decay constants of sinusoids making up said time-varying signal.

The impacts are imparted 1010 using an array of impactors (110) arranged on a line. When a line is completed (i.e., when all or selected ones of the impactors of the array have been activated) the sample is moved relative to the array of impactors in a direction substantially perpendicular to the line, and the array is activated again. This process is repeated iteratively until the entire surface of interest has been scanned. By proceeding in this manner, any anomalies (such as cracks, fissures or other material defects in the sample) can be localized with great precision.

The impact 1010 and capturing 1020 may be performed repeatedly, before the signals are analyzed 1030 (as illustrated, for example when the apparatus has multiple impactors operated consecutively), or alternatively, each captured signal may be analyzed separately.

Depending on the chosen excitory mode, the analyzing 1030 may further comprise determining a dynamic Young's modulus (E) or a shear modulus (G) from the frequencies in the spectrum of the response, in particular by identifying the peak frequency and applying a formula such as the ones provided above.

The further details and options provided above with respect to the apparatus according to the present invention also apply to the method according to the present invention.

Preferably, the analyzing further comprises comparing 1040 the decay constants to reference values. This step allows the method according to the present invention to be used for quality control purposes. Indeed, a method of controlling a quality of an article of manufacture, comprises characterizing at least a part of the article of manufacture as said solid material sample using the method described above, signaling a "pass" condition 1040/YES if the decay constants are within a predetermined margin of said reference values; and declaring a "fail" condition 1040/NO if the decay constants are outside said predetermined margin of said reference values.

The present invention also pertains to a computer program product comprising coding means configured to cause a processor to carry out the computation steps of the methods described above.

While the invention has been described hereinabove with reference to specific embodiments, this was done to clarify and not to limit the invention, the scope of which is to be determined by reference to the accompanying claims.

The invention claimed is:

1. An apparatus for analyzing a mechanical vibratory response of a solid material sample, the apparatus comprising:
supports configured to support said solid material sample at nodes of a vibration mode to be excited;

an array of impactors arranged on a line to impart an impact on respective well-defined points on the surface of said solid material sample and means to cause a relative movement of said solid material sample and said array of impactors in a direction substantially perpendicular to said line, or an array of impactors arranged in a grid;

a sensor configured to capture said mechanical vibratory response as a time-varying signal, subsequent to each impact of said array of impactors; and processing means configured to analyze said time-varying signal to determine the frequencies and decay constants of sinusoids making up said time-varying signal;

wherein the apparatus is configured to activate all or selected ones of said impactors consecutively along the line prior to moving the line relatively to the sample or consecutively along the grid.

2. The apparatus according to claim 1, wherein the processing means is further configured to detect a material defect in said solid material sample on the basis of said determined frequencies and decay constants.

3. The apparatus according to claim 1, further configured to cause a relative movement of said solid material sample and said array of impactors along two axes.

4. The apparatus according to claim 1, further comprising one or more of a temperature sensor, means to determine geometric properties of the solid material sample, and a scale.

5. The apparatus according to claim 1, wherein the sensor is equipped with means to illuminate a spot where the mechanical vibratory response is captured.

6. The apparatus according to claim 1, wherein the sensor is a contact-based sensor equipped with means to measure a force applied by the sensor on said solid material sample.

7. The apparatus according to claim 1, wherein said processing means is configured to solve a harmonic inversion problem by applying a general filter-diagonalization method.

8. A method of characterizing a solid material sample, the method comprising:

placing said solid material sample on supports coinciding with nodes of the vibration mode to be excited;

imparting an impact on a plurality of well-defined points on the surface of said solid material sample, by using an array of impactors arranged on a line and moving said solid material sample relative to said array of impactors in a direction substantially perpendicular to said line, or by using an array of impactors arranged on a grid;

capturing a mechanical vibratory response as a time-varying signal, subsequent to said imparting of each such imparted impact; and analyzing said time-varying signal to determine the frequencies and decay constants of sinusoids making up said time-varying signal;

wherein all or selected ones of said impactors are consecutively activated along the line prior to moving the line relatively to the sample or activated consecutively along the grid.

9. The method according to claim 8, further comprising detecting a material defect in said solid material sample on the basis of said determined frequencies and decay constants.

10. The method according to claim 8, further comprising moving said solid material sample relative to said array of impactors along two axes.

11. The method according to claim 8, further comprising estimating a location of a defect on the basis of said frequencies and decay constants obtained for different impact positions.

12. The method according to claim 8, wherein said analyzing further comprises determining a dynamic Young's modulus (E) from said frequencies.

13. The method according to claim 8, wherein said analyzing further comprises determining a shear modulus (G) from said frequencies.

14. The method according to claim 8, wherein said analyzing further comprises comparing said decay constants to reference values.

15. A method of controlling a quality of an article of manufacture, the method comprising:

wherein at least a part of said article of manufacture as said solid material sample using the method according to claim 14;

signaling a "pass" condition if said decay constants are within a predetermined margin of said reference values; and declaring a "fail" condition if said decay constants are outside said predetermined margin of said reference values.

16. The method according to claim 8, wherein said analyzing comprises solving a harmonic inversion problem by applying a general filter-diagonalization method.

17. A computer program product comprising code means configured to cause a processor to carry out the computation steps of the method according to claim 8.

18. The computer program product according to claim 17, wherein said code means comprises the Harminv program.

* * * * *